US008829904B2

(12) United States Patent
White et al.

(10) Patent No.: US 8,829,904 B2
(45) Date of Patent: *Sep. 9, 2014

(54) METHOD OF AND APPARATUS FOR IN-SITU MEASUREMENT OF DEGRADATION OF AUTOMOTIVE FLUIDS AND THE LIKE BY MICRO-ELECTRON SPIN RESONANCE (ESR) SPECTROMETRY (75) Inventors: James R. White, San Mateo, CA (US); Christopher John White, Palo Alto, CA (US)

(73) Assignee: Active Spectrum, Inc., Foster City, CA (US)

( * ) Notice: Subject to any disclaimer, the term of this patent is extended or adjusted under 35 U.S.C. 154(b) by 213 days.

This patent is subject to a terminal disclaimer.

(21) Appl. No.: 13/366,925

(22) Filed: Feb. 6, 2012

(65) Prior Publication Data

US 2012/0133364 A1 May 31, 2012

Related U.S. Application Data (62) Division of application No. 12/316,215, filed on Dec. 9, 2008, now Pat. No. 8,125,224, which is a division of application No. 11/590,522, filed on Oct. 31, 2006, now Pat. No. 7,589,529.

(60) Provisional application No. 60/736,264, filed on Nov. 14, 2005.

(51) Int. Cl.
*G01V 3/00* (2006.01)
*G01R 33/343* (2006.01)
*H01P 7/06* (2006.01)
*G01N 24/10* (2006.01)
*G01R 33/345* (2006.01)
*G01N 24/08* (2006.01)
*G01R 33/30* (2006.01)
*G01R 33/34* (2006.01)
*G01R 33/60* (2006.01)

(52) U.S. Cl.
CPC .............. *G01N 24/10* (2013.01); *G01R 33/343* (2013.01); *H01P 7/06* (2013.01); *G01R 33/345* (2013.01); *G01N 24/08* (2013.01); *G01R 33/307* (2013.01); *G01R 33/34* (2013.01); *G01R 33/60* (2013.01)
USPC .......................................... 324/321; 324/318

(58) Field of Classification Search
USPC ................... 324/321, 318, 322, 316
See application file for complete search history.

(56) References Cited

U.S. PATENT DOCUMENTS 3,140,993 A 7/1964 Roberts
4,360,776 A 11/1982 Bauman
(Continued)

FOREIGN PATENT DOCUMENTS

DE 198 34 939 2/2000
JP 2002 062271 2/2002

OTHER PUBLICATIONS

Chzhan, M., et al., "A Tunable Reentrant Resonator with Transverse Orientation of Electric Field forin VivoEPR Spectroscopy," Journal of Magnetic Resonance, Academic Press, Orlado, FL, US, vol. 137, No. 2, Apr. 1, 1999, pp. 373-378.

(Continued)

*Primary Examiner* — Louis Arana
(74) *Attorney, Agent, or Firm* — Tope-McKay & Associates (57) ABSTRACT A method of and miniaturized apparatus adapted for in-situ measurement of degradation of automotive fluids and the like by micro-electron spin resonance (ESR) spectrometry, wherein the use of a modulated constant magnetic field in an RF resonating variable frequency microwave cavity resonator through which a fluid sample is passed, enables direct detection of molecular changes in such fluid sample resulting from fluid degradation during use.

13 Claims, 9 Drawing Sheets (56) References Cited

U.S. PATENT DOCUMENTS

| | | | |
|---|---|---|---|
| 4,593,248 A | 6/1986 | Hyde et al. | |
| 5,233,303 A | 8/1993 | Bales et al. | |
| 7,253,641 B2 | 8/2007 | Knitt et al. | |
| 7,260,930 B2 | 8/2007 | Decou et al. | |
| 7,391,212 B2 | 6/2008 | Maier et al. | |
| 7,589,529 B1* | 9/2009 | White et al. | 324/316 |
| 7,868,616 B2* | 1/2011 | White et al. | 324/316 |
| 8,125,224 B2* | 2/2012 | White et al. | 324/316 |
| 2003/0155916 A1 | 8/2003 | Maier et al. | |
| 2007/0024289 A1 | 2/2007 | Knitt et al. | |

OTHER PUBLICATIONS

J. R. White, et al., "Octave-Tunable Miniature RF Resonators," IEEE Microwave and Wireless Components Letters. Vo. 15, No. 11, Nov. 2005.

White, J., "Micro-ESR for Airborne Soot Measurement," 2008 Diesel Engine-Efficiency and Emissions Research (DEER) Conference Presentations, [online] Aug. 4, 2008, Dearborn, Michigan, Retrieved from the Internet: http://www1.eere.energy.gov/vehiclesandfuels/resources/proceedings/2008_deer_presentations.html [retrieved Nov. 25, 2008], (Aug. 2008).

PCT International Search Report and the Written Opinion of the International Searching Authority for PCT/IB2006/003174, (2009).

* cited by examiner

METHOD OF AND APPARATUS FOR IN-SITU MEASUREMENT OF DEGRADATION OF AUTOMOTIVE FLUIDS AND THE LIKE BY MICRO-ELECTRON SPIN RESONANCE (ESR) SPECTROMETRY

PRIORITY CLAIM

This is a Divisional application of U.S. patent application Ser. No. 12/316,215, filed Dec. 9, 2008, entitled, "Method of and Apparatus for In-Situ Measurement of Degradation of Automotive Fluids and the Like by Micro-Electron Spin Resonance (ESR) Spectrometry", which is a Divisional application of U.S. patent application Ser. No. 11/590,522, filed Oct. 31, 2006, entitled, "Method of and Apparatus for In-Situ Measurement of Degradation of Automotive Fluids and the Like by Micro-Electron Spin Resonance (ESR) Spectrometry," issued as U.S. Pat. No. 7,589,529, which is a Non-Provisional application of U.S. Provisional Application No. 60/736,264, filed Nov. 14, 2005, entitled, "In-Situ Measurement of Automotive Fluids Degradation by Micro ESR Spectrometry."

BACKGROUND OF THE INVENTION (1) Field of Invention

The invention relates to the field of electron spin resonance (ESR) spectrometry, and more particularly to the use of such technology for measuring and diagnosing the real-time degradation and changes of automotive fluids such as engine oil and the like, in situ and during operating engine conditions and environments.

(2) Description of Related Art

The maintenance and monitoring of fluids in vehicles, engines, pumps, weapons and machinery (all hereinafter, for convenience, generically referred to as "vehicles") is vital to ensuring reliable operation. While there is no single sensor available that can monitor all fluids simultaneously, due to the wide variation in composition and fluid failure mechanisms, a suite of networked, miniaturized onboard vehicle fluid sensors can be envisioned for continuous, in-situ monitoring of fluid degradation. In the case of brake fluid and hydraulic fluid, the main mechanism for fluid degradation is humidity absorption, excess particulates (metal and sand), and solvent contamination. In-line hydraulic fluid humidity sensors are commercially available from several sources. In the case of engine coolant, increased acidity leads to corrosion in internal engine components. The pH monitoring of coolant is beneficial, and could be implemented using commercial sensors (e.g. Durafet III pH electrode from Honeywell), which could be packaged for use in vehicles by a third party. In the case of engine oil, there are dielectric [1, 2], viscosity, conductivity [3], chromatic modulation [4], x-ray fluorescence, infrared, and other sensors used to detect changes in the observable fluid properties [5]. Several sensor systems are available which examine changes in dielectric permittivity and viscosity of oil [22], as are vehicle-specific software systems that predict oil failure based on past driving conditions (deployed by General Motors) [6]. There are to date, however, no commercially-available sensors that provide a rigorous, real-time detection of the most fundamental chemical mechanism of engine lubricating oil failure, —the formation of free radicals by the breakdown of long hydrocarbon molecular chains in oil. Only the overall results stemming from these free radical-induced changes have heretofore been monitored in-situ, but not the direct detection of the free radicals themselves.

Onboard monitoring of lubricant engine oil degradation provides a reduction in engine wear and reduced maintenance costs for the end-user [6]. The net economic benefit of this optimized maintenance schedule can be very large. In the United States, over one billion gallons of motor oil are used each year; thus any reduction in oil usage can have a significant impact. In civilian automotive applications, engine oil is typically changed every 3000-7500 miles, while coolant, brake fluid and automatic transmission fluid are changed every 30 k-50 k miles. The economic benefit to the end user of optimized engine oil management may be greater than for other automotive fluids, both in reduced fluid costs and in reduced wear of engine components.

Using flexural mechanical structures similar to earlier U.S. Pat. Nos. 5,964,242, 6,914,785 and 7,025,324, the present invention proposes to optimize a miniature electron spin resonance (ESR) sensor for the detection particularly, though not exclusively, of molecular peroxy radicals in engine oil and related or other fluids. The breakdown of engine oil is indicated by a sharp increase in the concentration of damaging peroxy radicals ($RO_2$.) among others in the oil. Peroxy radicals are readily identified by electron spin resonance (ESR) spectroscopy and thus give a clear and direct indication of the engine oil condition.

Numerous systems have before been developed by auto manufacturers and others for improved automotive fluids management. Researchers have prototyped the use of viscosity sensors, dielectric sensors, chromatic sensors (sensing color changes), oil pH sensors, miniature fourier transform infrared spectrometers (FTIR) and x-ray fluorescence sensors, sensors of magnetic particles are of iron-derived and transition metal particles and combinations thereof. General Motors employs a computer model, which uses the car driving history, environmental conditions (temperature, humidity) and maintenance history to predict when the oil must be changed, without specialized sensors, although detailed data from millions of miles of road tests was required to create this computer model [6]. The present invention, however, differs from these approaches in a fundamental way: directly in situ sensing the molecular changes that occur in oil as a result of breakdown of the lubricant.

(3) Objects of Invention

A principal object of the present invention, accordingly, is to provide a new and improved method of and apparatus for monitoring lubricant and other oil degradation and the like that, unlike prior fluid monitoring and maintenance techniques, including those above discussed, uses improved electron-spin resonance (ESR) spectroscopy sensors and techniques to directly sense the molecular changes that occur in such fluids as a result of molecular breakdown therein.

A further object is to provide such novel sensors of small and miniature size, low cost and low power consumption and adapted for integration in automotive engine systems and the like.

A further object is to provide a novel miniaturized ESR sensor and spectrometer of more general use and with other fluids as well.

Still another object is the providing of such a novel sensor that is adapted for implementation in onboard vehicle fluid diagnostic sensor suites also embracing one or more of pH, dielectric, temperature and humidity sensors and including microwave sensors of moisture content of the oil or other fluid and also the presence of ferromagnetic particles and the like.

Other and further objects will be later detailed and are also delineated in the appended claims.

SUMMARY OF THE INVENTION

In summary, and in one of its broader methodology aspects, the invention embraces a method of using electron spin resonance spectrometry for measuring the degradation of vehicle fluids, that comprises, passing a sample of such fluid through a resonating variable RF frequency microwave cavity resonator during the application therethrough of a constant magnetic field;

rapidly modulating the magnetic field correspondingly to vary the resonant magnetic susceptibility in such fluid sample;

modulating the RF frequency of the cavity resonator in accordance with such magnetic susceptibility variation; and measuring such RF frequency modulation or amplitude modulation thereof to derive an electron spin resonance signal that directly senses the molecular changes in the fluid sample resulting from fluid degradation during operation of the vehicle.

In its novel apparatus context, the invention provides an electron spin resonance sensor particularly adapted for use as a spectrometer having, in combination, a broadly frequency-swept high Q tunable microwave cavity resonator, provided with a fluid inlet and an outlet in its walls for internally passing a fluid sample through the resonator during the resonating of the cavity resonator by microwave energy in order to effect absorption or dispersion of the microwave energy in the sample, and wherein the cavity resonator is disposed in an external uniform permanent magnetic field of sufficient intensity to cause magnetic resonance in the sample within the range of frequency sweeping.

In a still further preferred apparatus embodiment, the cavity resonator is of re-entrant toroidal configuration sandwiched between opposing permanent magnet structures and with a piezoelectric means extending along the top of the toroid, with a capacitance gap being formed externally of the cavity between a surface of the re-entrant configuration and a proximate surface. The resonator and magnetic field-producing structure is of miniaturized stacked construction and adapted to be mounted onboard, in situ with operating machinery, such as on board a vehicle or other machinery monitoring the degradation of lubricant oil and other fluids.

Preferred and best mode embodiments and designs are hereinafter presented in detail.

BRIEF DESCRIPTION OF THE DRAWINGS

The invention will now be described with reference to the accompanying drawings in which.

DETAILED DESCRIPTION

(1) Description of Preferred Embodiment(s) of Invention

Before proceeding to describe preferred sensor structures and circuits for practicing the invention, it is believed to be helpful briefly to review the principles and prior implementation of electron spin resonance (ESR) spectrometry.

(2) Specific Details (2.1) Electron Spin Resonance (ESR) Spectrometry

Figure 5:
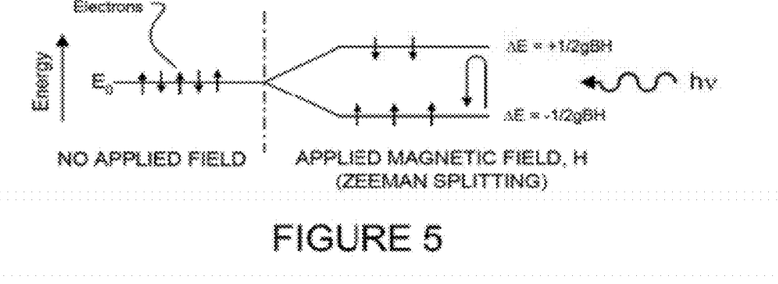
FIG. 5 is an explanatory diagram of electron energy transitions stimulated in a sample of the oil under incident microwave energy and in an applied magnetic field, showing the Zeeman splitting effect under such magnetic field.

An electron spin resonance (ESR) spectrometer detects the concentration and composition of free radicals present in, for example, an oil sample. The sample is loaded into a high frequency microwave resonant cavity in a magnetic field H. Free radicals irradiated with microwave radiation will undergo transitions at a characteristic frequency governed by the following equation (1), and as shown conceptually in FIG. 5 which shows the before-mentioned Zeeman-effect splitting under the applied magnetic field:

$$h\nu = gBH \tag{1}$$

Figure 9:
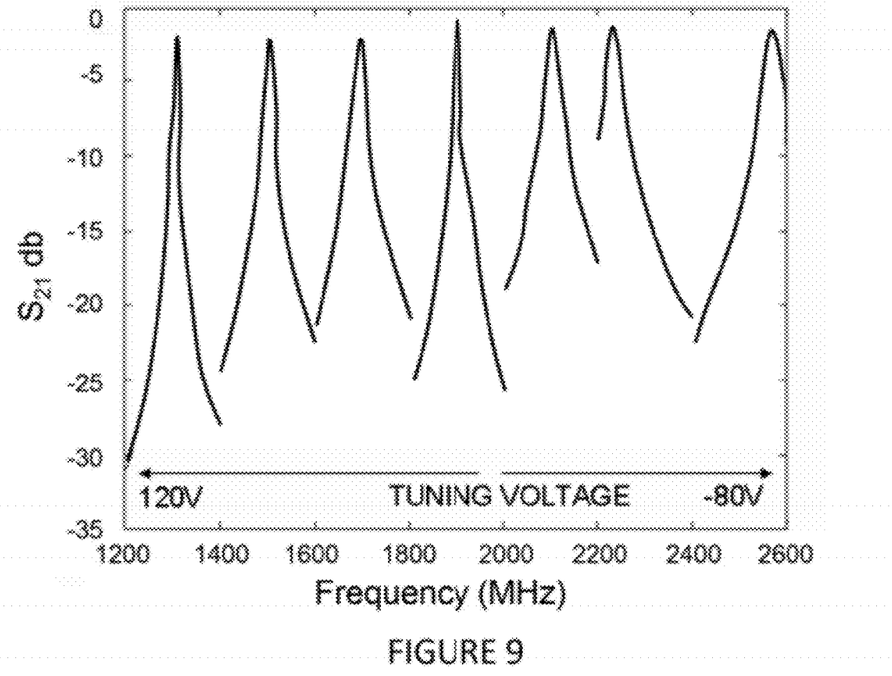
FIG. 9 is a graph of an experimentally obtained passband response for broad tuning of a prototype sensor over a 1.3-2.6 GHz microwave band.

In this equation, h is Planck's constant, B is the Bohr Magneton, v is the resonant frequency, H is the applied magnetic field, and g is a characteristic of the radical (the "g-factor," a number, often close to 2.0000). The absorption of incident microwave energy has a characteristic resonant peak, as shown in FIG. 9. The frequency (or magnetic field) at resonance is a function of the g-factor, and the height of the resonant peak is determined by the concentration of the radical in the sample.

Historically (since 1945), ESR spectrometers have used large electromagnets to generate a variable magnetic field, and have employed fixed-frequency cavities. This is a similar arrangement to that found in a nuclear magnetic resonance (NMR) spectrometer. In terms of portability, this design has been a significant hindrance since the tunable electromagnet magnet assembly weighs upwards of 200 kg and requires water cooling and several kW of power for operation. The micro-ESR sensor of the present invention has circumvented this problem by using a small, strong permanent magnet assembly such as of rare-earth elements or other permanent constant field magnets that generate a fixed, uniform magnetic field (700 Gauss, for example), together with a broadly tunable (not fixed-frequency) microwave cavity (tunable from 1.3 to one hundred percent higher 2.6 GHz, for example, as in FIG. 9). This broadly tunable, high-Q cavity resonator is an enabling technology in the micro-ESR sensor design and operation of the invention.

(2.2) Structural and Electrical Design

Figure 1:
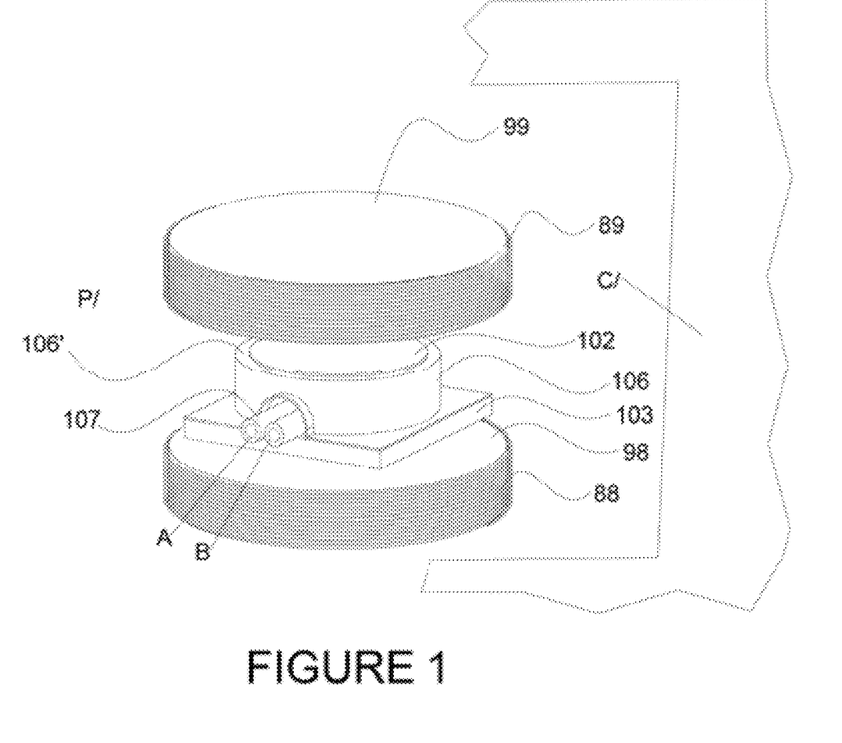
FIGS. 1 and 2 are exploded isometric views of internal components of a miniaturized micro-ESR continuous flow-through oil or similar fluid sensor of molecular changes that occur as a result of fluid breakdown in usage, and constructed in accordance with a preferred embodiment of the invention.
Figure 2:
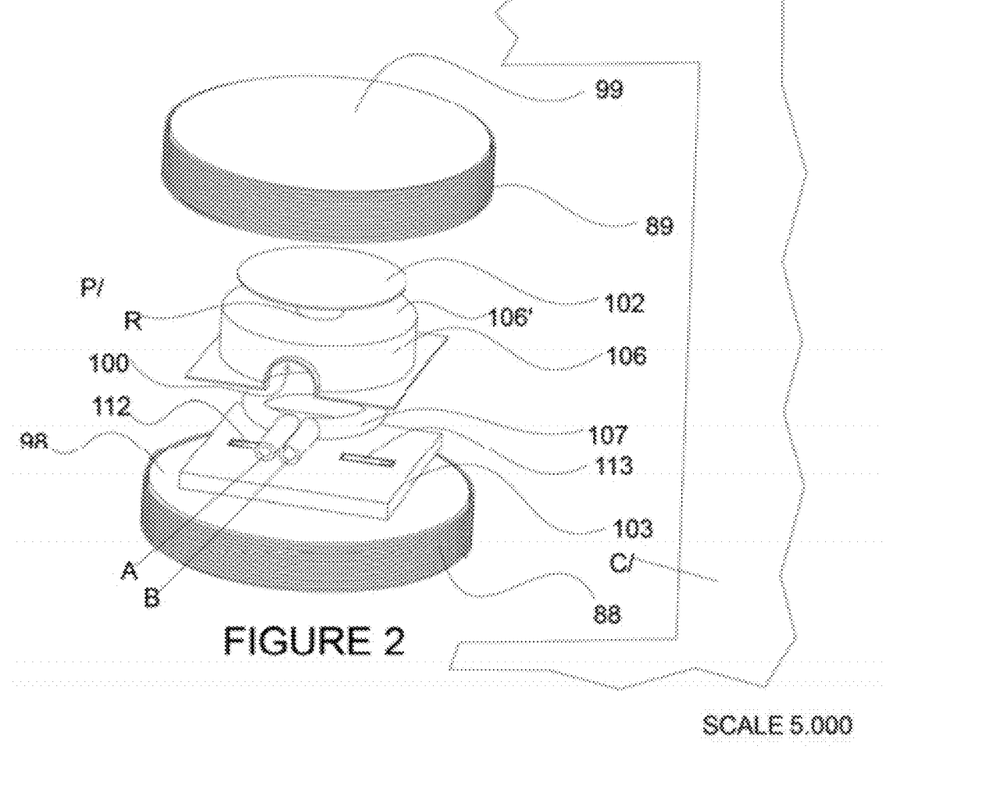
Figure 3:
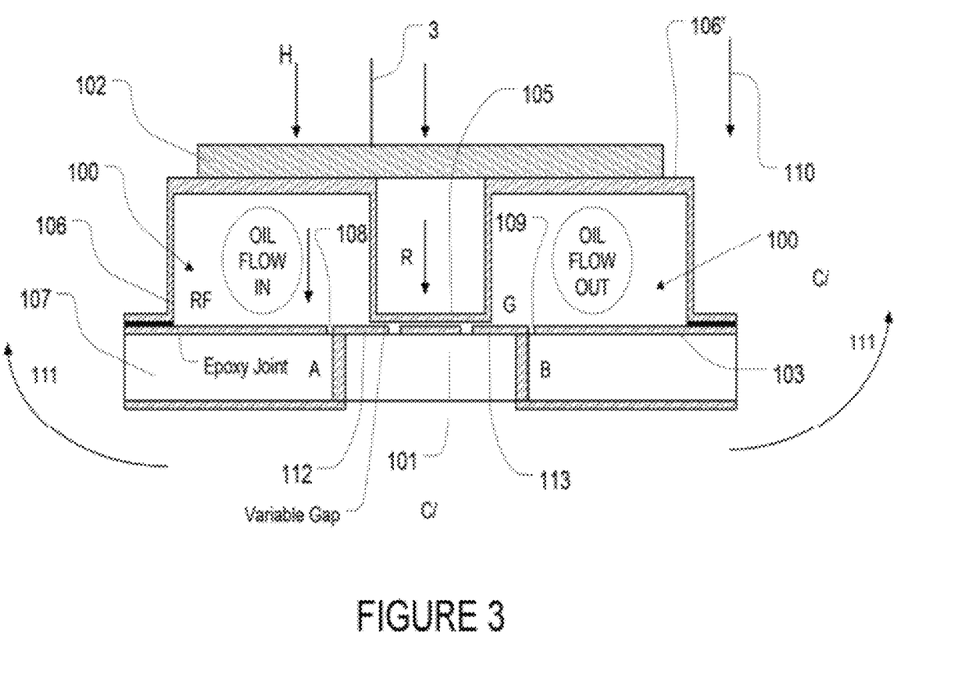
FIG. 3 is a cross-sectional view on a somewhat larger scale of the sensor portion of FIGS. 1 and 2.

Turning, now, to the sensor construction of the present invention as illustrated in the cross-sectional view of FIG. 3 and the isometric exploded views of FIGS. 1 and 2, a sandwich type stacked assembly package P is provided wherein preferably a toroidal-shaped integral conductive-walled chamber 106 bounds internally a microwave resonant toroidal annular cavity chamber 100 excited in conventional well-known manner at RF excitation feed 112 as schematically represented at RF. The cavity, as before mentioned, is covered along the top wall 106¹ by an attached planar electric-to-mechanical transducer such as a piezoelectric disc element or film 102, and rests along the bottom on an integral conductive planar base plate 103, similarly to structures taught in our copending U.S. patent application Ser. No. 11/392,980, filed Mar. 28, 2006 for a Variable Electrical Circuit Component and in our later-referenced IEEE article. Under the present invention, however, a sample of the fluid-to-be-monitored, such as the before-mentioned exemplary engine oil or lubricant, is carried into one side of the cavity (shown as the top left A in FIGS. 1 and 2), passed through the cavity and flowing out the other side B through a dielectric fluid tubing loop 107 inserted within the cavity. The bottom of the re-entrant center column R of the toroidal chamber 106 is closed by a wall 105, as taught in the before-referenced US patents, (sometimes referred to by the trade name Aesop "Nanogate" technology) closely positioned to left- and right-hand electrical coupling structures 108-112 and 109-113 on opposite sides of the center portion 101 of the base 103, as more particularly shown in FIG. 3, wherein the slot 113 serves as the RF output probe feed. The elements 105 and 101 define a gap G serving as a capacitor in the overall resonating circuit, with the toroidal cavity 100 serving as the inductance of the resonating circuit.

Figure 6:
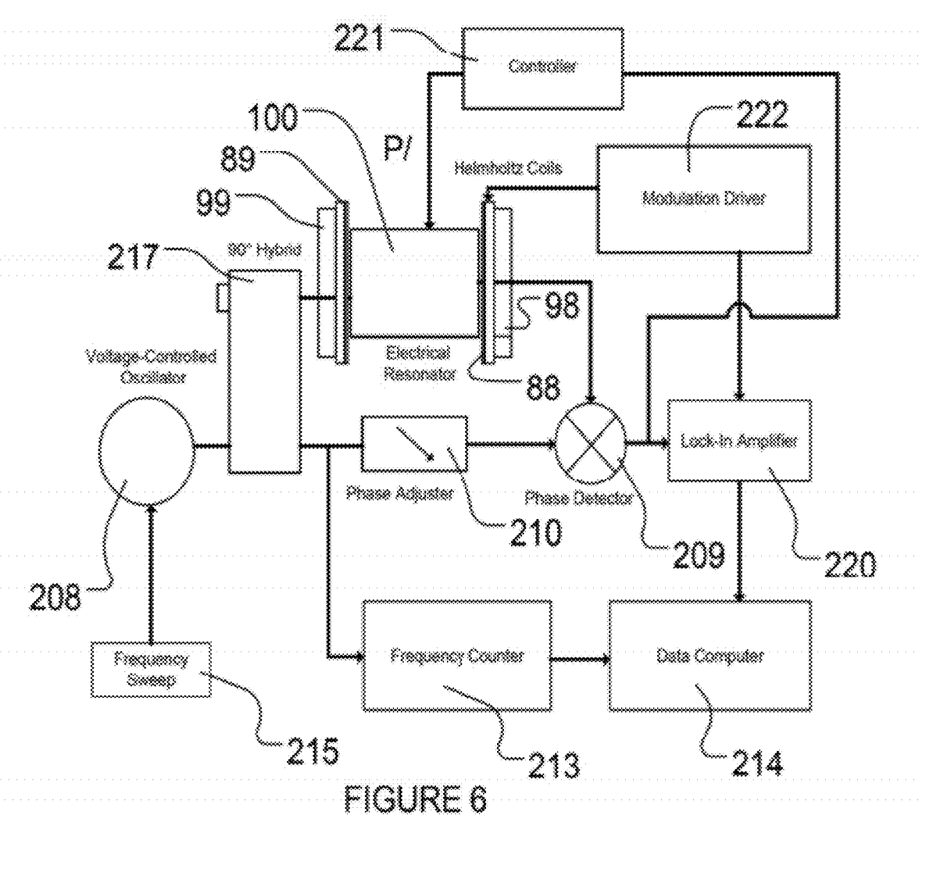
FIGS. 6 and 7 are block diagrams illustrating preferred details of electrical sensing designs of the mini-ESR spectrometer system of the invention.

At the top of the cylindrical sandwich sensor unit P, above the piezoelectric element 102, a preferably circular permanent magnet 99 is externally mounted (FIGS. 1 and 2), and at the bottom, below the plate 103, it acts with an opposing similar magnet 98 to set up the earlier-mentioned uniform, fixed or constant magnetic field H passing through the annular cavity 100 in the vertical-arrowed direction 110. Magnetic field modulating Helmholtz-type coils 88 and 89 may also be provided for rapid modulation of the magnetic field (for example at a frequency of about 10 KHz) to provide for synchronous detection of magnetic resonance as later explained. The magnetic coil modulation frequency may typically be between 1 KHz and 100 KHz. Below 1 KHz, vibrations tend to reduce the spectrometer sensitivity. At more than 100 KHz, the synchronous detector (lock-in amplifier) later discussed in connection with the system of FIG. 6 is difficult to implement using linear circuits. The fluid sample itself, moreover, has a finite response time which would limit the maximum magnetic field modulation frequency. The return fixed magnetic field flux path is along the outer casing of the whole instrument (schematically represented at C), along the arrows 111 in FIG. 3, with the casing C preferably constructed of a material with high magnetic permeability such as mild steel or the like.

When the piezoelectric disc or film 102 at the top wall of the toroidal resonant chamber deforms—contracts or expands—in response to applied voltage at 3, it flexes the top wall 106¹ as an elastically deformable diaphragm and thus flexes the toroidal cavity shape, causing variation of the gap spacing G of the before-described external capacitance defined between the center bottom wall portion 105 and the opposing wall 101 of the base 103, and thus providing variable capacitance tuning of the resonating circuit. The integral constraining cavity side walls act as an elastic fulcrum mechanically supporting the outer edge of the cavity flexible top wall 106¹, such that the vertical force produced in the central region R by the expansion or contraction of the piezoelectric disc 102 creates amplified enhanced tuning displacements in the gap G. The structure of the resonant cavity 100-106 thus itself provides an elastically deformable fulcrum which is deformed by the piezoelectric actuator 102, and serves to amplify the motion of the cavity top surface 106¹ in a manner similar to that described in said patents.

The invention therefore uses a permanent constant magnetic-field-producing assembly stacked with and passing a magnetic field through the cavity resonator 100-106 while its conductive internal cavity space is electrically resonating at an RF microwave frequency with its integral but external capacitive gap G. The return magnetic flux path, as before stated, is the outer instrument casing C. This is in direct contrast to prior-art ESR detectors which, as earlier mentioned, have employed varying (not fixed) magnetic fields that require the before-mentioned large-size magnetic-field generating coils, and are used with a fixed (not variable) cavity resonant frequency, necessitating the very large-size construction of the prior ESR systems. Through the use of the permanent magnets of fixed field and external variable capacitor with a very small gap, miniaturization of the stacked structure of the present invention is enabled, and this, in turn, makes possible an on-board in-situ mounting and use at the engine.

Figure 4:
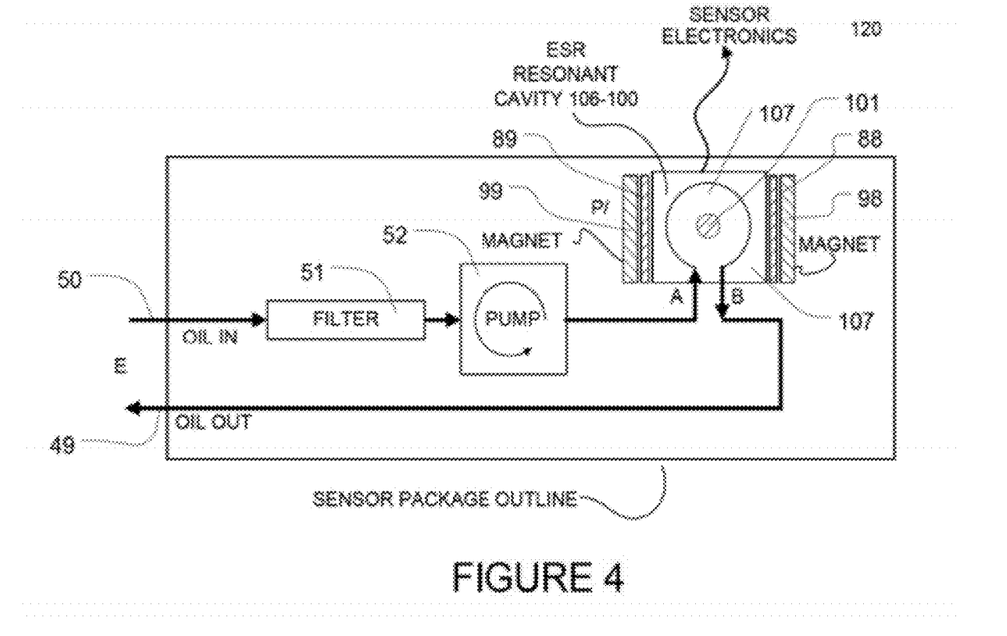
FIG. 4 is a block diagram showing a complete oil degradation sensing package and system.

The installation of the sensor package stack P of the invention in an exemplary oil degradation sensor system is shown in FIG. 4, wherein a small pump 52 drives oil from the engine E at 50 ("oil in") into the inlet A and through the hollow tubing loop 107 inside the resonant cavity 100, exiting at B and 49 ("oil out") such that a sample of the oil (or other fluids) can be continuously introduced into and withdrawn from the sensor in a controlled and continuous pass-through manner. A lower cost gravity-fed design or an arrangement where the sensor is fitted to pressurized oilways in the engine may also be used. An in-line filter 51 may prevent clogging of the tubing (2 mm ID fine tubing, for example) in the resonator assembly. By making a sensor with larger internal channels, a filter may indeed be rendered unnecessary. The overall miniaturized sensor package of FIG. 4 may be about two inches wide and one inch high.

(2.3) Breakdown of Engine Oil

Oxidation of petroleum hydrocarbons proceeds by a radical chain mechanism via alkyl and peroxy radicals after an induction period wherein the antioxidants in the oil are consumed. The chain is initiated as follows:

$RH \rightarrow R.(\text{free radical}) + H.$ $RH + O_2 \rightarrow R.(\text{free radical}) + HO_2.$ The chain then propagates as:

$R. + O_2 \rightarrow RO_2.(\text{peroxy radical})$ $RO_2 + R'H \rightarrow ROOH(\text{hydroperoxide}) + R'.$ Oxidation reactions can result in premature degradation of the base fluid (i.e. the formation of acids, gums, lacquers, varnishes and sludges) at prolonged high temperatures. Mineral oil fractions already contain natural inhibitors in the form of sulphur and nitrogen compounds, aromatics or partially hydrogenated aromatics, phenolic oxidation products, etc., which delay oxidation and impart good ageing properties. However, when the mineral oil is subjected to a high degree of refining, these materials can be lost along with those having less desirable characteristics [18].

(2.4) Exemplary ESR Spectrometer Systems

In FIG. 6, a 90° hybrid 217, the electrical cavity resonator package P-100, a phase adjuster 210, and a phase detector 209 are shown arranged as a frequency discriminator circuit. Frequency modulation of the resonator cavity 100 causes phase modulation of the RF signal coupled through it. The phase modulation of the RF carrier is demodulated by the phase detector 209 which may be implemented as a mixer operating with the RF and the inputs from a local oscillator 208, in quadrature. The oscillator phase is adjusted at 210 for such quadrature phase detection.

The spectrometer operates via a slow frequency sweep (so-labeled at 215) of the voltage-controlled local oscillator (VCO) 208. A low bandwidth integrator servo loop is used with a controller 221 to adjust the cavity electrical resonator frequency to the frequency of the voltage-controlled oscillator 208. The bandwidth of the servo loop may, however, in some instances, be too slow in this type of embodiment to compensate phase modulation by the magnetic modulation field introduced by the Helmholtz coils at 88 and 89. The sensor piezo driver is thus within the servo loop that adjusts the frequency of the resonant cavity 100 to the frequency of the swept oscillator 208. The bandwidth of this loop is on the order of Hz, such that it does not respond to changes in magnetic resonance caused by the modulation field.

Magnetic resonance causes a change in the magnetic susceptibility of the oil sample passed through the cavity resonator at a frequency depending on the Zeeman field at the fluid sample (FIG. 5). The modulation of the magnetic field applied by the modulation driver and Helmholtz coils (~0.1-10 Gauss amplitude) varies the Zeeman field at the sample and therefore the frequency of magnetic resonance. At a given measurement frequency, the modulation of the magnetic susceptibility of the fluid sample modulates the RF frequency of the cavity resonator. The frequency modulation of the cavity resonator is measured by the above-described frequency discriminator circuit, including the frequency counter 213 inputting a data computer 214, and synchronously detected at baseband using the servo loop and lock-in amplifier 220 also feeding the data computer 214, all schematically represented in FIG. 4 as the "sensor electronics 120". Such measurement provides an electron spin resonance signal that directly indicates the molecular changes in the fluid samples resulting from fluid degradation during operation of the vehicle.

Figure 7:
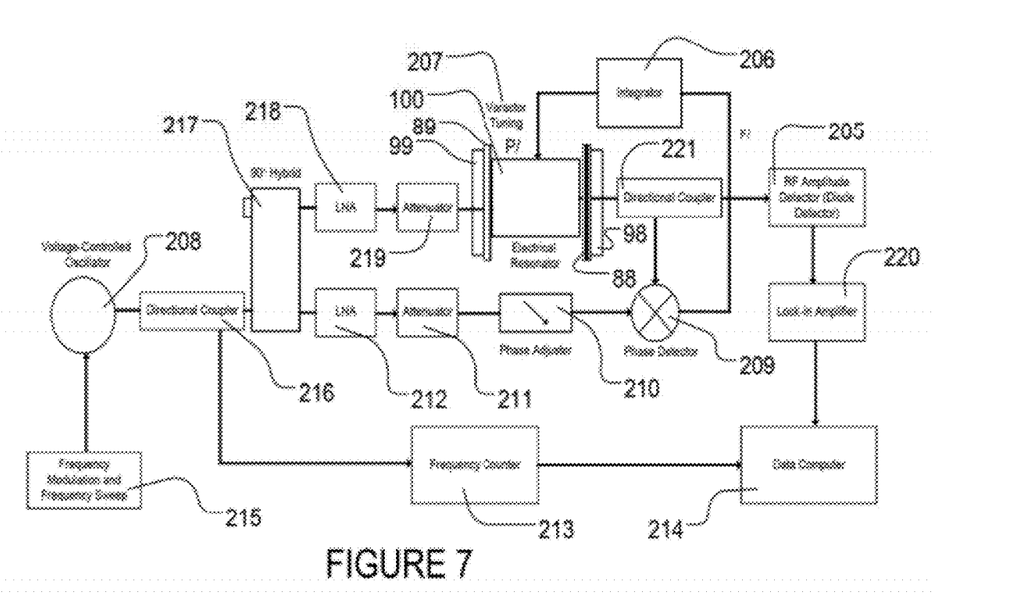

In a second implementation shown in FIG. 7, frequency modulation of the RF carrier is used spectrometrically to detect resonance in the magnetic susceptibility of the fluid sample. In this design, the integrator-servo bandwidth is larger than the modulation frequency, so that the electrical cavity resonator frequency tracks the modulation of the frequency swept voltage-controlled oscillator 208. As before stated, this circuit uses the integration (206) servo feedback loop F and also varactor tuning 207 as labeled. Magnetic resonance is detected via changes in insertion loss of the cavity resonator, which causes amplitude modulation of the RF carrier. The RF signal amplitude modulation is demodulated at 205 and synchronously detected using the before-mentioned phase lock-in amplifier 220.

The signal from the phase detector is used to lock the cavity resonator frequency to the frequency modulation of the voltage-controlled oscillator 208. The RF amplitude detector 205 measures changes in the insertion loss of the cavity resonator 100 which are caused by the paramagnetic resonance absorption of the oil sample passed through the loop 107 in the cavity resonator 100. The system requires careful matching and power leveling of the VCO signal to avoid spurious AM background. Additional components, such as directional couplers 218, 221, attenuators 219, 211 buffer amplifiers and isolators, may be used to improve the design, if desired.

The design of the frequency-swept ESR spectrometer of the invention is thus fundamentally different from that of conventional ESR spectrometers since the quantity measured is both phase dispersion and amplitude variation. The spectrometer is a novel variation in which the electron spin resonance signal is detected via the amplitude modulation of the transmission coupled RF carrier, since the automatic frequency control loop is configured to follow the frequency modulation of the VCO 215-208.

The preferred RF frequency tuning mechanism for the invention is shown based on the before-mentioned "Nanogate" mechanical diaphragm flexure of the cavity top wall $106^1$ in response to the action of the piezoelectric element 102 and is used to precisely tune the spacing G between the capacitor electrodes 105-101 of the sensor, FIG. 3.

Figure 8:
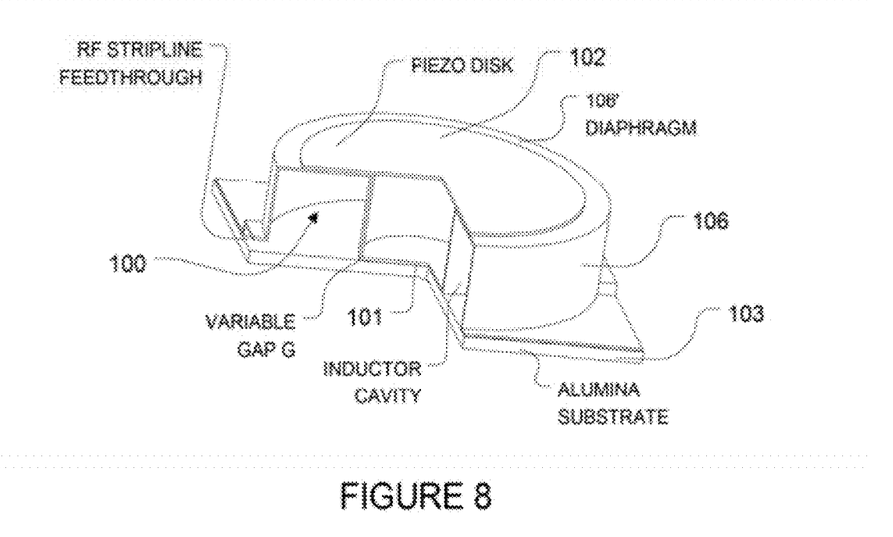
FIG. 8 is an isometric view partly cut-away of a preferred cavity resonator construction for the sensor.

Recent experimental work has demonstrated that a simple, tunable LC resonator structure of this type, FIG. 8, which uses a piezoelectric drive 102 and has miniature dimensions approximately 13 mm by 13 mm by 3 mm height, enables very broad tuning and with high-Q over a 1.3-2.6 GHz band, and a quality factor of 380. This is the type of structure we have described in our article "Octave-Tunable Miniature RF Resonators" appearing in the IEEE Microwave and Wireless Components Letters, Vol. 15, No. 11, pages 793 on, November 2005. As shown in FIG. 9, the center frequency of the resonator can be continuously varied to any frequency between, in this case, 1.3 GHz and 2.6 GHz, by adjusting the voltage applied at 3 to the piezoelectric actuator 102.

(2.5) Sensitivity Considerations

Considering, now, the achievable sensitivity of sensors constructed in accordance with the present invention, an experimental comparison of the sensitivity of the mini-ESR spectrometer of the invention to the typical sensitivity of a classic relatively fixed-frequency 10 GHz X-band EPR spectrometer design, demonstrated that, the sensitivity is equal or better for limited sample sizes. The key parameters in comparing the sensitivity of different spectrometer designs are the resonator quality factor Q, the fill factor η, and the dielectric loss of the sample. The result of the analysis is that while X-band cavities have very high-Qs (~5000), the sensitivity in most practical cases is on par with smaller re-entrant high-Q cavity type resonators because the fill factor is much larger for re-entrant cavities. This result is well documented in the literature on ESR (e.g. [8, 9, 10]) and explains the increasing use of loop-gap and re-entrant type resonators:

Re-entrant cavity and loop-gap resonators have Qs of the order of 500, but much larger fill factors than X-band cavity resonators. For limited sample sizes or aqueous samples, the sensitivity of loop-gap resonators is equivalent or better than traditional X-band cavity resonators [8, 9, 10]. The exception is for large samples of low loss dielectric. The Octave+ resonators are ideal for use in the ESR detection of the invention due to the combination of high-Q (~500) and a small volume. In addition, the isolation of the magnetic field region within the cavity 100 from the external capacitive gap G reduces the sensitivity of the cavity to dielectric loss, which is important for fluid samples containing water. X-band cavities have dramatically reduced Q for large samples containing water. Even for small samples, placement at the center of the cavity (node in the electric field for a $TE_{102}$-excited cavity) is essential to minimize the degradation of the cavity Q due to such dielectric loss.

The fill factor for a $TE_{102}$ mode X-band cavity is:

$$\eta = \frac{2V_s}{V_c} \quad (2)$$

where $V_s$ is the sample volume and $V_c$ is the cavity volume, in the range of 10 cc [11]. A typical sample volume is in the range of 0.1 cc, which means that the fill factor for an X-band cavity is in the range of 2% in practice. In contrast, loop-gap and re-entrant cavity resonators are designed for much higher fill factors at small sample volumes [12, 13, 14, 15, 7]. The Octave+ tunable resonators are ideal to achieve a combination of large fill factor and high-Q, quality factor, which may be compared to X-band cavities and conventional loop-gap resonators as in Table 1 below:

TABLE 1

|  | X-Band | Loop-Gap | Octave+ Tunable Resonator |
|---|---|---|---|
| Quality Factor Q | 5 000 | 500 | 500 |
| Fill Factor η | 2% | 20% | 30% |
| FOM Sensitivity | 100 | 100 | 150 |

As mentioned above, the ESR sensitivity is proportional to the product of the fill factor and Q, and the performance of different spectrometers can be compared using the product of these two parameters, as also shown in Table 1. Loop-gap resonators have sensitivity on par with X-band cavities for typical samples, and for the Octave+ tunable resonator, a 50% improvement in sensitivity is expected because of the careful optimization of the quality factor and resonator volume. Again, the sensitivity comparison of cavity and loop-gap resonators is well known in ESR research [8, 9, 10].

In practice, an RF microwave cavity design where the large electric and large magnetic field regions are segregated, as in the construction of FIGS. 1, 2 and 3 of the invention, is important to realize a high-Q resonator. Dielectric absorption of the RF electric field via water molecules in the sample decreases the resonator Q. Only the RF magnetic field, however, excites magnetic resonance. In reference to the before-described FIG. 8, the "inductive" region of the re-entrant cavity 100 is the internal toroidal chamber space or region containing the sample. In this region, the magnetic field is large and the electric field is small. The "capacitive" region, as before explained, where the electric field is most intense, is the capacitive gap G, external to the cavity. Thus, in the re-entrant cavity design of the invention, the effect of dielectric absorption in the fluid sample in the cavity-Q is minimized by restricting or confining or isolating the placing of the sample to or in the inductive internal cavity region 100 only. The overall fill factor may still be large, however, since the resonant energy is stored equally in the magnetic and electric fields.

The absolute sensitivity of a spectrometer in terms of the measurable number of spins can be quantified by calculating the amplitude and phase modulation introduced by paramagnetic resonance. The effective inductance L of the loop-gap resonator or other resonator containing the paramagnetic sample is modified by the change in magnetic susceptibility as given by the expression:

$$L = L_0[1+4\pi\eta(\chi'-i\chi'')] \quad (3)$$

where $\chi'$ and $\chi''$ are the real and imaginary parts of the magnetic susceptibility (i.e. dispersion and absorption.) The fill factor η is ratio of RF magnetic field stored in the fluid sample and the magnetic field in the entire cavity:

$$\eta = \frac{\int_{sample} H_1^2 \, dv}{\int_{cavity} H_1^2 \, dv} \quad (3A)$$

The fluid sample contained in the resonant circuit results in a perturbation to the frequency and loss of the cavity. The phase perturbation introduced by paramagnetic resonance by a signal coupled in transmission is:

$$\partial\theta = -4\pi\theta Q_L \chi' \quad (4)$$

and the change in the resonator quality factor due to magnetic resonance is:

$$\frac{\Delta Q}{Q_L} = -\frac{Q_L}{Q_L + Q_M} \cong -\frac{Q_L}{Q_M} = 4\pi\eta Q_L \chi'' \quad (5)$$

where $Q_L$ is the loaded-Q of the electrical resonator. The paramagnetic resonance frequency is modulated by using the Helmholtz coils to modulate the Zeeman field. The phase and amplitude perturbations described by equations (4) and (5) can be used to calculate the power of the phase and amplitude modulation introduced on the RF microwave carrier by the magnetic resonance absorption. This sideband power is equated to the noise floor of the receiver to find the minimum detectable number of spins:

$$N_{min} = \frac{V_s}{4\pi\eta Q_L} \frac{kT}{(g_s\mu_B)^2} \frac{\Delta v}{v_0} \sqrt{\frac{kT}{P_s}} \quad (6)$$

where $P_s$ is the carrier power, $\Delta v$ is the ESR resonance width, and $v_o$ is the ESR resonant frequency. For example, using typical parameters, assume a 0.1 cc sample volume, $Q_L=500$, fill factor /1;4, and a 5 Gauss line at 1000 Gauss field:

$$N_{min} = \frac{0.1 \text{ cc}}{4\pi \cdot 0.25 \cdot 500} \frac{1}{8.29e-27} \frac{5}{1000} \sqrt{\frac{4.14e-21 \text{ J} \cdot 1 \text{ Hz}}{10^{-3} \text{ W}}} = \quad (7)$$
$$3.84 \times 10^{19} \cdot 2 \times 10^{-9} = 7.8 \times 10^{10}$$

Equation (7) is the "rule of thumb" sensitivity of $10^{11}$ spins/mT for ESR spectrometers, i.e., for a 10 Gauss ESR resonance, the minimum measurable number of spins is $10^{11}$ in a 1 Hz bandwidth. For some spectrometer designs, the phase and amplitude noise of the microwave source and vibrations, may be limiting factors for the sensitivity. However, with refinements to the design, sensitivity limited by the thermal noise floor of the receive chain can be realized (c.f. [7] for complete discussion)

(2.6) Permanent Magnet Design

Figure 10:
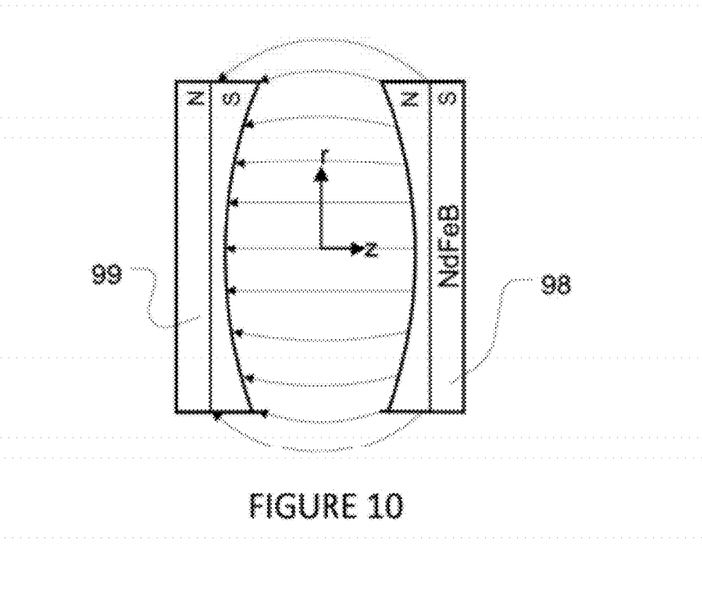
FIG. 10 is a diagram of a preferred design of a permanent magnet assembly with uniform magnetic field in accordance with the invention.

As before explained, the feature of being able to use permanent magnets for miniaturization and other purposes requires, however, careful design of the shape and positioning of the permanent magnets in the sensor assembly P in order to maximize the sensitivity of the sensor. One approach is to grind the faces of the magnets with a curved shape as in [16] and FIG. 10, which extends the region of field homogeneity substantially. For the present invention, a low-frequency finite-element modeling program called Maxwell™ may be used numerically to optimize the shape of the magnet face, as shown conceptually in FIG. 10. Rare earth NdFeB or other permanent magnets 98, 99 may be custom-ground to the optimized shape. In high-volume production, the field magnets would be sintered directly with the optimal curved face, thus the final cost in production would be little more than for flat-faced magnets.

(2.7) Experimental Results

Figure 11:
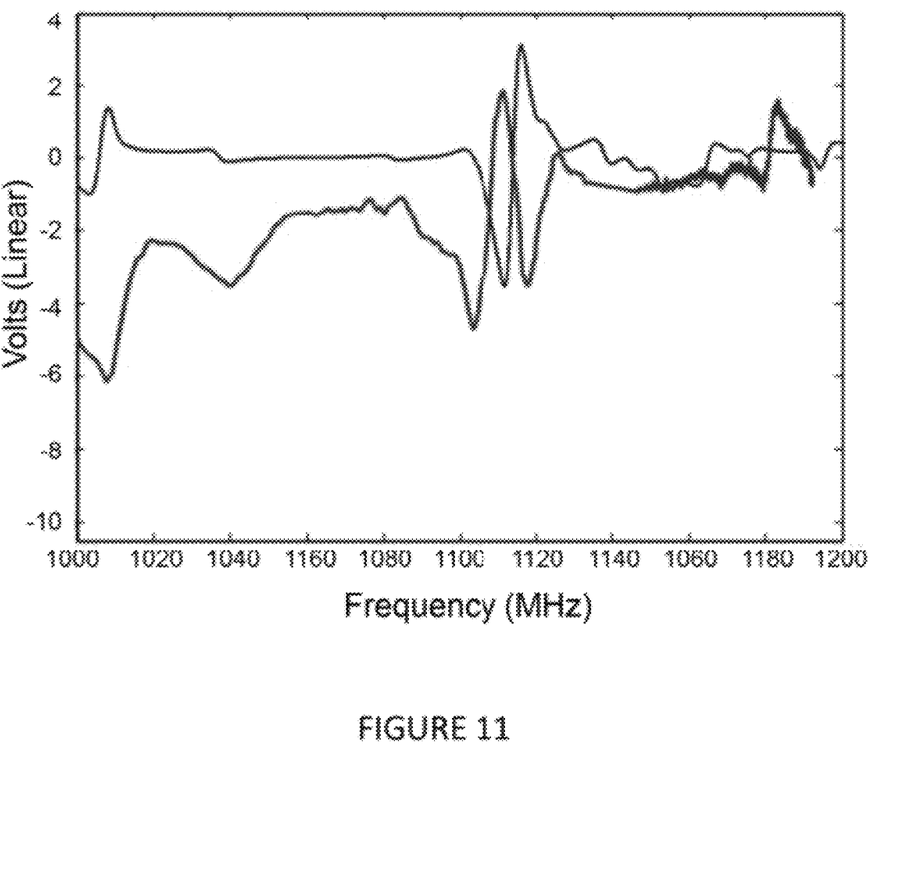
FIG. 11 presents a sample of the signal output from a zero-field miniature ESR spectrometer of the type shown in FIG. 7.

In order to provide a baseline reference for a pure oil "signature" to serve as a basis for comparison with deteriorating oils in the field, ESR spectrum performance at a zero reference magnetic field must be known. A sample of the signal output from the zero-field miniature ESR spectrometer of the present invention is shown in FIG. 11. This is the spectrum from a Vanadium-doped Magnesium Oxide crystal placed in the cavity resonator 100.

Figure 12:
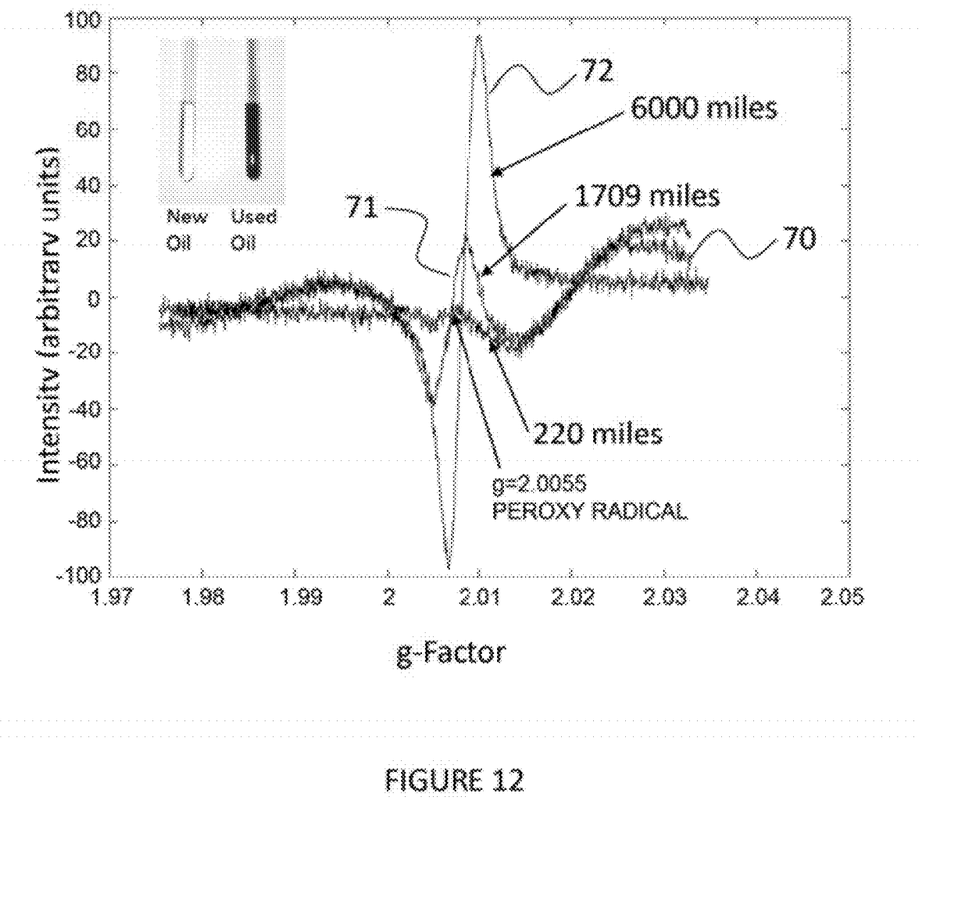
FIG. 12 presents signal-processed experimentally obtained intensity vs. g-factor graphs of an X-band (9.80 GHz) ESR spectrum obtained for new and used motor oil.

Experimental investigation results of the radical concentrations in used engine oil are shown in FIG. 12. Engine oil from a brand-new 2005 Chrysler Sebring at 220 mi. and 1709 mi, and an additional sample of used oil (used for 6000 miles) from a 1990 Honda Accord were obtained and tested in a Bruker Biospin ESR. The experiment used X-band (9.80 GHz) ESR spectra of new and used motor oil. All samples showed the characteristic ESR signal at g=2.0055 corresponding to the peroxy radical responsible for oil breakdown [19]. An additional signal corresponding to carbon radicals was also observed, which shifts the zero-crossing of the ESR signal, as shown. Signal-processing techniques were employed to separate the signal due to carbon radicals from the signal due to the peroxy radical. In this case, each signal can be approximated as the first derivative of a Lorentzian curve, and given the overall peak width, peak height, zero-crossing point, and the g-values of each radical, with a simple iterative algorithm determining the best fit for each radical species.

In the course of this specification, bracketed numbers have been used to refer to published reference materials of relevance. These are now summarized in the following tabulation:

[1] A. A. Carey and A. J. Hayzen, CSI, "The Dielectric Constant and Oil Analysis". *Practicing Oil Analysis* Magazine, September 2001.

[2] R. D. Lee, H. J. Kim, Y. P. Semenov, "Capacitive Sensor for in situ Measurement of Deterioration of Car Engine Oil," *The Korean Sensors Society*, Vol. 10, No. 4, pp. 266-272, 2001.

[3] Basu, A. et al: "Smart Sensing of Oil Degradation and Oil Level Measurements in Gasoline Engines," SAE Technical Paper 2000-01-1366, SAE World Congress, Detroit Mi Mar. 6-9, 2000.

[4] I. I. Khandaker, "A fibre-optic oil condition monitor based on chromatic modulation," *Meas. Sci. Technol.* 4 (1998) 608-613.

[5] J. D. Turner and L. Austin, "Electrical techniques for monitoring the condition of lubricating oil,"*Meas. Sci Technol.*, 14 (2003) 1794-1800.

[6] B. W. Wilson et. al. "Development of a modular in-situ oil analysis prognostic system," *Int. Soc. Logist. Symp., pp.* 1999.

[7] C. White, "A Solid-State Atomic Frequency Standard" Ph.D Thesis, California Institute of Technology, 2005.

[8] A. J. Hoff ed., *Advanced EPR: applications in biology and biochemistry*, Elsevier, Amsterdam, 1989, p. 282.

[9] S. Pfenninger et al., "Bridged Loop-gap Resonator: A resonant structure for pulsed ESR transparent to high-frequency radiation," *Rev. Sci. Instrum.*, 59, 752, 1988.

[10] W. Piasecki, W. Froncisz, and James S. Hyde, "Bimodal Loop-gap Resonator," *Rev. Sci. Instrum.*, 67, 1896, 1996.

[11] Charles P. Poole, Electron Spin Resonance: A Comprehensive Treatise on Experimental Techniques, 2nd ed., Wiley 1983, c.f. p 395.

[12] S. Pfenninger, W. Froncisz, J. Forcer, J. Luglia, and James S. Hyde, "General Method for Adjusting the Quality Factor of EPR Resonators," *Rev. Sci. Instrum.*, 66, 4857, 1995.

[13] T. Christides, W. Froncisz, T. Oles, James S. Hyde, "Probehead with Interchangeable Loop-gap Resonators and RF Coils for Multifrequency EPR/ENDOR," *Rev. Sci. Instrum.*, 65, 63, 1994.

[14] W. Froncisz and James S. Hyde, "The Loop-gap Resonator: A New Microwave Lumped Circuit ESR Sample Structure," *J. Magnetic Resonance*, 47, 515, 1982.

[15] W. N. Hardy and L. A. Whitehead, "Split-ring Resonator for use in Magnetic Resonance from 200-2000 MHz," *Rev. Sci. Instrum.*, 52, 213, 1981.

[16] Rupp, L. W. et al, "Miniature magnet for electron spin resonance experiments," Am. J. Phys. V. 44, no. 7, July 1976, pp. 655-657.

[17] A. H. Price and G. H. Wegdam, "Dielectric spectroscopy at microwave frequencies,"*J. Phys. E*, vol. 10, pp. 478-481, 1977.

[18] "Emission Scenario Document on Lubricants and Lubricant Additives," OECD, www.oecd.org/ehs/, December 2004.

[19] Ikeya, M. "Car Mileage Determination with ESR Signal of Engine Oil: A Case of Organic ESR Dating," ESR Dating and Dosimetry, IONICS, Tokyo, 1985, pp. 453-457.

[20] J. W. Waters et. al., "Remote Sensing of Atmospheric Water Vapor and Liquid Water with the Nimbus 5 Microwave Spectrometer;" *J. Appl. Meteo.*, vol. 15 pp. 1204-1208, 1976.

[21] Aesop Inc. Datasheet for Octave+2.5-5.0 Ghz miniature tunable resonator, www.activespectrum.com, 2005.

[22] D. R. Sparks et. al. "Application of MEMS Technology in Automotive Sensors and Actuators," *Init. Symp. Micromech. And Human Sci., pp.* 9-16, 1998.

[23] U.S. Pat. No. 4,803,624, issued Feb. 7, 1989, to Pilbrow et al., discloses a portable electron spin resonance spectrometer.

[24] Hiroshi Hirata, Toshifumi Kuyama, Mitsuhiro Ono, and Yuhei Shimoyama, "Detection of electron paramagnetic resonance absorption using frequency modulation," Journal of Magnetic Resonance, 164 (2003) 233-241.

While the invention has been described with particular reference to the important application for in situ on-board monitoring of the state of degradation of vehicle engine fluids, the novel ESR sensor construction of the invention may also be usefully employed with other fluids and materials and in a myriad of other applications including in other fields; and further modifications will therefore occur to those skilled in this art, such being considered to fall within the spirit and scope of the invention as defined in the appended claims.

What is claimed is:

1. A method of using electron spin resonance spectrometry for measuring the degradation of vehicle fluids, that comprises, passing a sample of such fluid through a resonating variable RF frequency microwave cavity resonator during the application therethrough of a constant magnetic field;

producing magnetic resonance that changes the magnetic susceptibility of the fluid sample at a frequency depending on the Zeeman field thereat;

rapidly modulating the magnetic field correspondingly to vary the frequency of magnetic resonance and correspondingly to vary the magnetic susceptibility in the fluid sample;

modulating the RF frequency of the cavity resonator in accordance with such magnetic susceptibility variation; and measuring the RF frequency modulation or resulting amplitude modulation thereof to derive an electron spin resonance signal that directly senses the molecular changes in the fluid sample resulting from fluid degradation during operation of the vehicle.

2. The method of claim 1, wherein said RF frequency modulation of the cavity resonator causes phase modulation of the RF signal coupled therethrough, and such phase modulation is thereupon detected.

3. The method of claim 2, wherein the phase modulation detection is effected by phase quadrature detection with a frequency-swept-voltage-controlled oscillator, with the RF cavity resonator frequency being servo-loop adjusted to the frequency of the oscillator.

4. The method of claim 3, wherein the modulation of the magnetic field varies the Zeeman field at the fluid sample correspondingly to vary the frequency of said magnetic resonance and thus the variation in the magnetic susceptibility of the fluid sample, with the modulating of the RF cavity resonator frequency being effected in accordance with such variation of the magnetic susceptibility.

5. The method of claim 1, wherein the RF frequency modulation is used to detect resonance in the magnetic susceptibility of the fluid sample.

6. The method of claim 5, wherein magnetic resonance in the fluid sample is detected by changes in the insertion loss of the cavity resonator which produces amplitude modulation of the RF frequency and results from paramagnetic resonance absorption of the fluid sample passed through the cavity resonator; and demodulating and synchronously detecting the RF amplitude modulation.

7. The method of claim 1, wherein, the microwave resonance of the cavity is produced by resonating inductance provided by the internal cavity space within the cavity resonator, with capacitance provided external to said space.

8. The method of claim 7, wherein the fluid sample is passed through the internal cavity space and is isolated from the external capacitance and its electric field.

9. The method of claim 7, wherein said capacitance is provided at a gap below and external to the internal cavity of the resonator.

10. The method of claim 9, wherein the varying of the RF frequency of the cavity resonator is effected by varying the gap of the external capacitance.

11. The method of claim 10, wherein the varying of the gap is effected by mechanically deforming the cavity resonator in response to the variation of the magnetic susceptibility.

12. The method of claim 11, wherein the mechanical deforming is effected by a piezoelectric element positioned along the top wall of the cavity resonator, and wherein an electrical signal varying in accordance with the variation of the magnetic susceptibility is provided to the piezoelectric element.

13. The method of claim 1, wherein the cavity resonator and the apparatus for producing the constant magnetic field and its modulating are miniaturized, stacked, and mounted in situ on the vehicle.

* * * * *